United States Patent
Forssmann et al.

(10) Patent No.: US 6,326,163 B1
(45) Date of Patent: Dec. 4, 2001

(54) METHOD FOR THE DIRECT DIAGNOSTIC DETECTION OF GENETICALLY CAUSED PATHOGENIC POINT MUTATIONS

(75) Inventors: Wolf-Georg Forssmann; Manfred Raida; Bernhard Brenner; Volker Nier, all of Hannover (DE)

(73) Assignee: Pharis Biotec GmbH, Hannover (DE)

( * ) Notice: Subject to any disclaimer, the term of this patent is extended or adjusted under 35 U.S.C. 154(b) by 0 days.

(21) Appl. No.: 09/147,404
(22) PCT Filed: Jun. 20, 1997
(86) PCT No.: PCT/EP97/03241
§ 371 Date: Apr. 6, 1999
§ 102(e) Date: Apr. 6, 1999
(87) PCT Pub. No.: WO97/49993
PCT Pub. Date: Dec. 31, 1997

(30) Foreign Application Priority Data

Jun. 21, 1996 (DE) .............................. 196 24 802

(51) Int. Cl.$^7$ ................. C12Q 1/00; C12Q 1/37
(52) U.S. Cl. ................. 435/24; 435/4; 435/968
(58) Field of Search .................. 435/24, 4, 968

(56) References Cited

U.S. PATENT DOCUMENTS

| | | | |
|---|---|---|---|
| 5,208,458 | 5/1993 | Busch et al. | 250/288 |
| 5,429,923 | 7/1995 | Seidman et al. | 435/6 |

FOREIGN PATENT DOCUMENTS

| | | |
|---|---|---|
| WO 95/25281 | 3/1995 | (WO) . |
| WO 95/33856 | 6/1995 | (WO) . |

OTHER PUBLICATIONS

Eckardstein et al., *The Journal of Biological Chemistry*, "Structural Analysis of Human Apolipoprotein A–I Variants", vol. 265, No. 15, pp. 8610–8617, 1990.

Falick et al, *Rapid Communications in Mass Spectrometry*, "Tandem Mass Spectrometry in the Clinical Analysis of Variant Hemiglobins", vol. 4, No. 10, pp. 396–400, 1990.

Murray et al., *Analytical Chemistry*, "Liquid Sample Introduction for Matrix–Assisted Laser Desorption Ionization", pp. 2534–2537, Sep. 15, No. 18, 1993.

Griffin et al, *International Journal of Mass Spectrometry and Ion Processes*, "Structural analysis of proteins by capillary HPLC electrospray tandem mass spectrometry", 111 (1991) pp. 131–149

Davis et al., *266th Analytical Chemistry*, "A Microscale Electrospray Interface for On–Line, Capillary Liquid Chromatography/Tandem Mass Spectrometry of Complex Peptide Mixtures", 67 (1995) Dec. 15, No. 24.

*Primary Examiner*—Louise N. Leary
(74) *Attorney, Agent, or Firm*—Jacobson Holman, PLLC

(57) ABSTRACT

The present invention relates to a quick method for the qualitative and quantitative medical-diagnostic analysis on the protein level of the substitution of single amino acids with pathogenic and non-pathogenic effects on the organism. The medical-diagnostic analysis is performed by a combination of enzymatic or chemical cleavage of the isolated peptide, chromatographical separation of the fragments and analysis by mass spectrometry, both direct LC/MS and indirect MALDI-MS, and analysis by capillary electrophoresis. By comparing protein samples from healthy humans with those of ill humans, the method described is suitable for establishing new, as yet unknown mutations and quantifying the expression and incorporation of wild type to mutant.

8 Claims, 9 Drawing Sheets

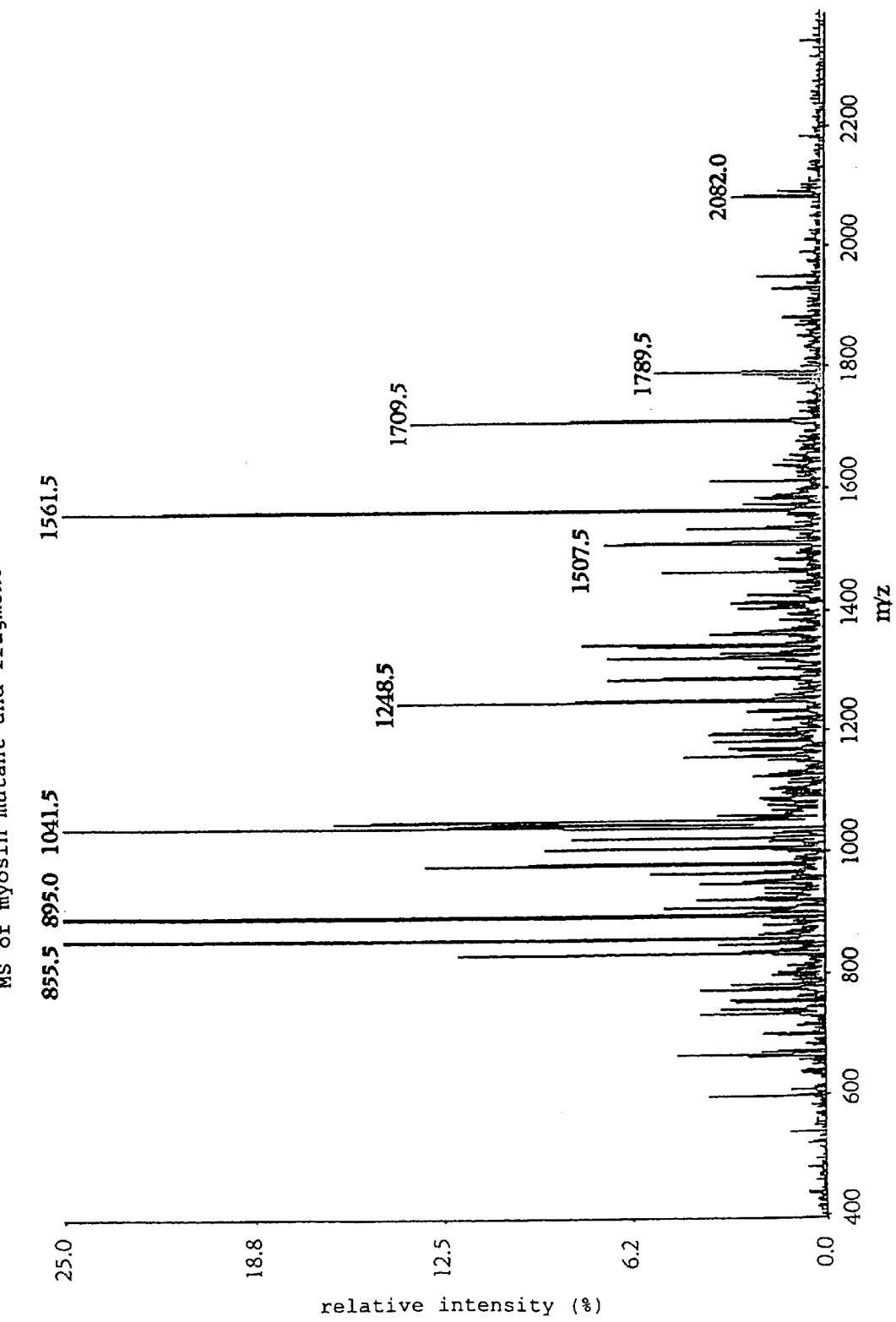

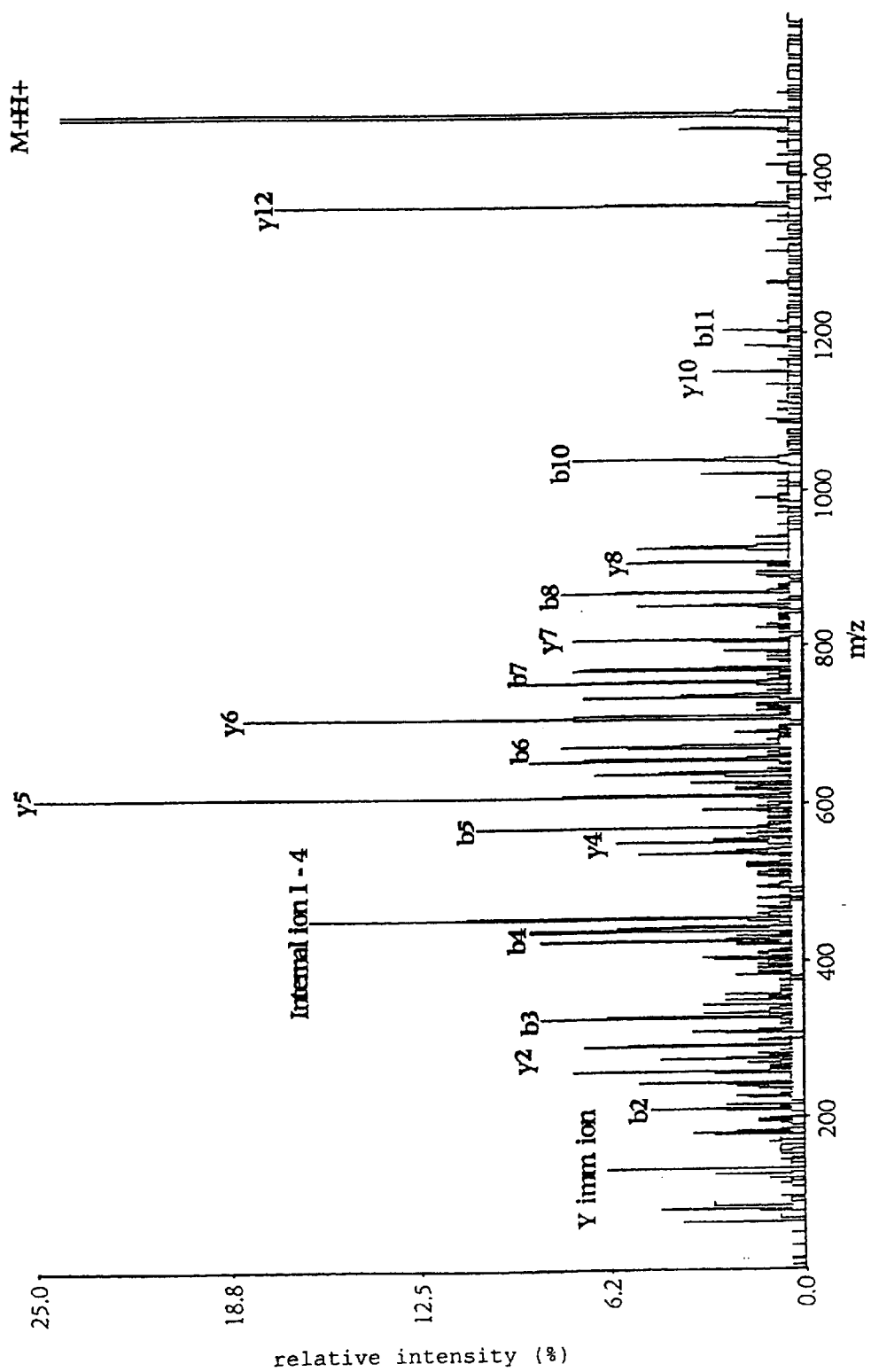

FIG. 5 detected fragments of β-myosin

Figure 1A:
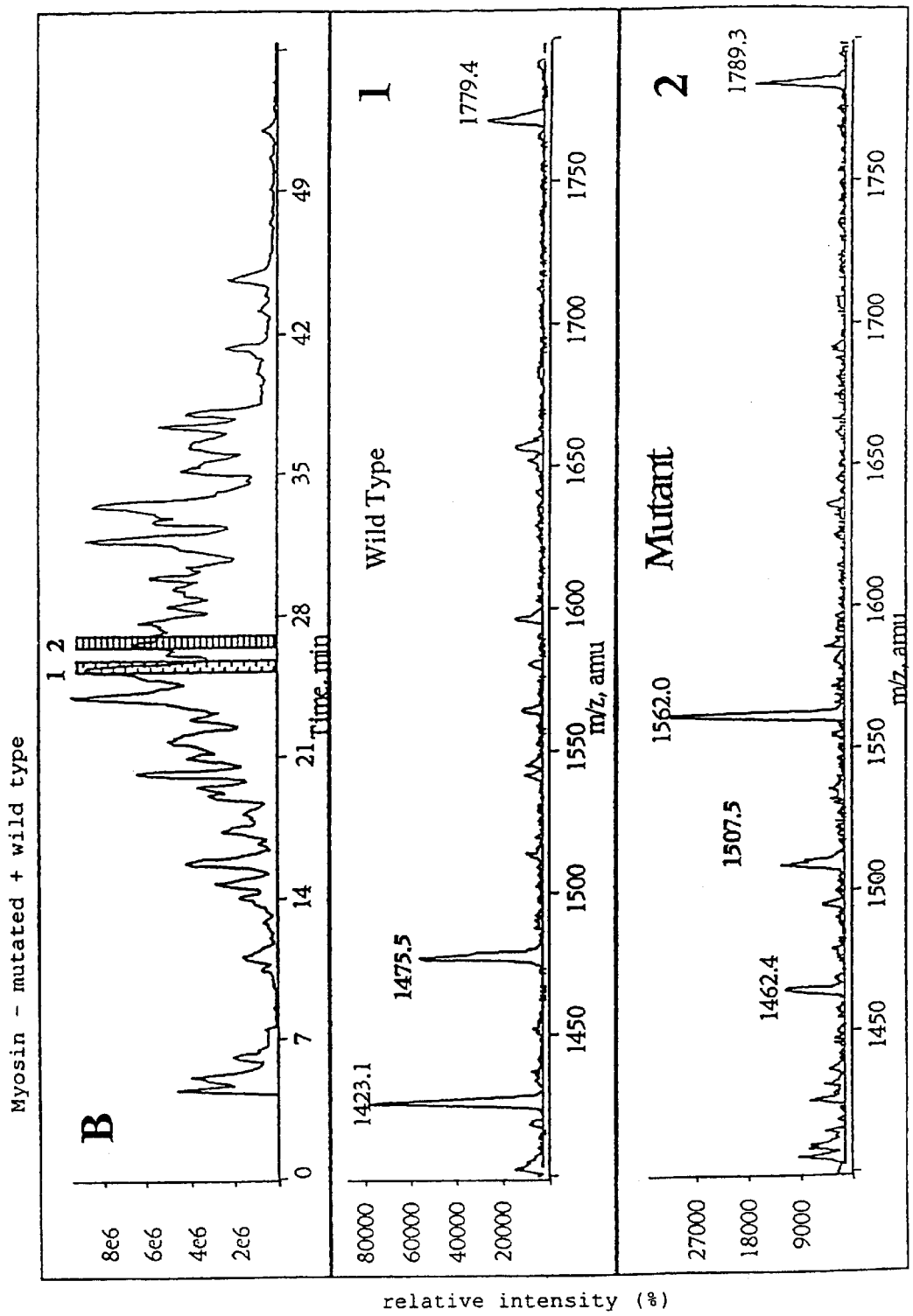

```
0001 MGDSEMAVFG AAAPYLRKSE KERLEAQTRP FDLKKDVFVP DDKQEFVKAK IVSREGGKVT AETEYGKTVT VKEDQVMQQN
                                   V                                                   I
0081 PPKFDKIEDM AMLTFLHEPA VLYNLKDRYG SWMIYTYSGL FCVTVNPYKW LPVYTPEVVA AYRGKKRSEA PPHIFSISDN
                                                                          Q
0161 AYQYMLTDRE NQSILITGES GAGKTVNTKR VIQYFAVIAA IGDRSKKDQS PGKGTLEDQI IQANPALEAF GNAKTVRNDN
0241 SSRFGKFIRI HFGATGKLAS ADIETYLLEK SRVIFQLKAE RDYHIFYQIL SNKKPELLDM LLITNNPYDY AFISQGETTV
                              Q          E
0321 ASIDDAEELM ATDNAFDVLG FTSEEKNSMY KLTGAIMHFG NMKFKLKQRE EQAEPDGTEE ADKSAYLMGL NSADLLKGLC
0401 HPRVKVGNEY VTKGQNVQQV IYATGALAKA VYERMFNWMV TRINATLETK QPRQYFIGVL DIAGFEIFDF NSFEQLCINF
        Q                                                            C
        L
        W
0481 TNEKLQQFFN HHMFVLEQEE YKKEGIEWTF IDFGMDLQAC IDLIEKPMGI MSILEEECMF PKATDMTFKA KLFDNHLGKS
                                          C
0561 ANFQKPRNIK GKPEAHFSLI HYAGIVDYNI IGWLQKNKDP LNETVVGLYQ KSSLKLLSTL FANYAGADAP IEKGKGKAKK
                                                    S M                N
                                                    R V
0641 GSSFQTVSAL HRENLNKLMT NLRSTHPHFV RCIIPNETKS PGVMDNPLVM HQLRCNGVLE GIRICRKGFP NRILYGDFRQ
                                                                                           R W
0721 RYRILNPAAI PEGQFIDSRK GAEKLLSSLD IDHNQYKFGH TKVFFKAGLL GLLEEMRDER LSRIITRIQA QSRGVLARME
        C           L M                   R                              G                 T
                        W
0801 YKKLLERRDS LLVIQWNIRA FMGVKNWPWM KLYFKIKPLL KSAEREKEMA SMKEEFTRLK EALEKSEARR KELEEKMVSL
                                                                                          H
0881 LQEKNDLQLQ VQAEQDNLAD AEERCDQLIK NKIQLEAKVK EMNERLEDEE EMNAELTAKK RKLEDECSEL KRDIDDLELT
                  V                             K                                 K
0961 LAKVEKEKHA TENKVKNLTE EMAGLDEIIA KLTKEKKALQ EAHQQALDDL QAEEDKVNTL TKAKVKLEQQ VDDLEGSLEQ
1041 EKKVRMDLER AKRKLEGDLK LTQESIMDLE NDKQQLDERL KKKDFELNAL NARIEDEQAL GSQLQKKLKE LQARIEELEE
```

METHOD FOR THE DIRECT DIAGNOSTIC DETECTION OF GENETICALLY CAUSED PATHOGENIC POINT MUTATIONS

The present invention relates to a method according to the generic part of claim 1.

Mutations on the gene level often cause inappropriate amino acids to be incorporated in proteins which are encoded in the corresponding gene segment which has mutated. This may result in pathologic phenomena, e.g., sickle-cell anaemia. Examinations of the presence of mutations which are responsible for pathologic conditions are usually performed on the DNA level. Such examinations are cumbersome, and their evaluation takes very long as a rule.

Thus, an object of the invention has been to provide a method by which the presence of mutations can be established quickly and reliably.

According to the invention, this object is achieved by a method with the features as defined in claim 1.

The method according to the invention serves to recognize mutations in organisms by comparing a deviation, Caused by a mutation, of the amino acid composition of a protein expressed in the region of the mutation (protein to be examined) with a corresponding protein which is expressed by a wild type lacking the mutation. The method according to the invention is characterized in that a sample is taken from the organism at a site where the protein to be examined is expressed, can be detected and/or plays a physiological role;

either the protein is concentrated or purified by methods of protein analysis, followed by a determination of its molecular weight, or a determination of the molecular weight of the protein to be examined is performed without a pretreatment of the sample.

The invention advantageously relates to a quick method for a qualitative and quantitative medical-diagnostic analysis on the protein level of the substitution of single amino acids with pathogenic or non-pathogenic effects on the organism. The medical-diagnostic analysis is preferably performed by a combination of enzymatic or chemical cleavage of the isolated peptide, chromatographical separation of the fragments and analysis by mass spectrometry, both direct LC/MS and indirect MALDI-MS, and analysis, e.g., by capillary electrophoresis. By comparing protein samples from healthy subjects with those of ill subjects, the method described is suitable for establishing new, as yet unknown mutations and quantifying the expression and incorporation of wild type to mutant.

The obtaining of samples from an organism, especially by biopsy, can be considered a basis of the method according to the invention. As the sites where the samples are taken, sites are selected in which the protein to be examined is expressed, detectable or plays a physiological role, e.g., in muscle fiber bundles or tissue pieces from organs, especially hearts. The samples are advantageously processed in such a way that the substitution of a single amino acid can be unambiguously detected by mass-spectrometric, chromatographical and/or electrophoretical methods, and the expression and incorporation ratio of wild type to mutant can be quantitatively determined. Thus, it becomes possible by a direct protein analysis as well to diagnose the causes of a genetically caused disease at an early stage and to identify as yet unknown mutations by a comparative analysis of samples from healthy subjects and samples from ill subjects.

By using the highly sensitive "matrix-assisted laser-induced desorption and ionization time-of-flight mass spectrometry" (MALDI-MS) in combination with liquid chromatography, especially using columns with an inner diameter of $\leq 1$ mm (microbore and capillary columns), the detection can be effected even with minute sample quantities.

As compared to the as yet performed analyses of the DNA coding for the proteins, the method is characterized in that the detection of the mutation and the determination of the expression and incorporation ratio is effected in a significantly shorter period of time. An analysis can be performed within one week, in contrast to the usual times required for DNA analysis, ranging from several weeks to half a year.

It is an advantage that a specific cleavage of the protein recovered from biopsy samples for diagnostic purposes is performed with selective enzymes, endoproteinases, or by chemical reagents, and the fragments obtained by such cleavage are separated by chromatographical methods and characterized in terms of their molecular weights either directly (LC/MS) or indirectly (MALDI-MS). The distribution in the separation and the molecular weight, determined by mass spectrometry, is unambiguous evidence for each fragment of the protein.

With smaller proteins, i.e., those having a molecular weight of up to 100,000 Dalton, the amino acid substitutions can be directly determined with the method described, without a preliminary cleavage into fragments. The accuracy of the measurement enables the precise determination of deviations in molecular weight of <5 Dalton and thus the detection of both wild type and mutant in the presence of each other. The precise localization of the amino acid substitution can be effected by the above described cleavage.

Thus, it is possible to characterize all proteins involved in a physiologically functional structure, e.g., muscle, in terms of genetically caused pathogenic and non-pathogenic amino acid substitutions.

Since the amino acid sequences of a lot of proteins are already known due to the sequencing of the human genome and all human proteins will be elucidated in a few years, a protein can be analyzed for mutations by means of the method herein described by selecting the appropriate cleavage which can be achieved by one skilled in the art by per se known methods.

It can be of great importance that this method may also be adapted for clinical-diagnostic use in the recognition of the causes of diseases and, through an optimization of the separation and detection conditions, also for the systematic screening of patient samples for particular, defined mutations.

Using appropriate equipment, the method described may also be automated to a large extent. For the procedure as described, the duration of an analysis is in the range of a few days whereas DNA analysis takes several weeks to months. At the same time, all proteins involved in a physiologically functional structure can be analyzed by this method.

Unlike the conventional methods for the detection of point mutations by analyzing the genomic DNA or cDNA, this method allows the quantification of the expression and incorporation of the mutant in the physiologically functional structure, especially if, due to the presence of a diploid set of chromosomes in the nucleus, both forms of the respective protein are expressed and it is not known in what ratio the two forms are present in the functional form.

The invention further allows evidence of the identity of the wild type and of the mutant to be furnished by chemical sequence analysis or by amino acid analysis.

A preferred embodiment of the method according to the invention comprises the cleavage of the protein to be examined with suitable enzymes or chemical reagents, and a combination of chromatographical methods, especially high-pressure liquid chromatography with capillary columns (MB-HPLC), and mass spectrometry.

The invention will be further illustrated by using the heavy chain of the β-isoform of myosin as an example. Point mutations in the heavy chain of the ⊖-isoform of myosin, e.g., substitution of the amino acid methionine for the amino acid valine in position 606, may result in hypertrophic cardiomyopathy, a genetically caused thickening of certain heart walls which may lead to sudden death. According to the invention, the detection of the mutation is possible by a combination of enzymatic cleavage and LC/MS.

Figure 1B:
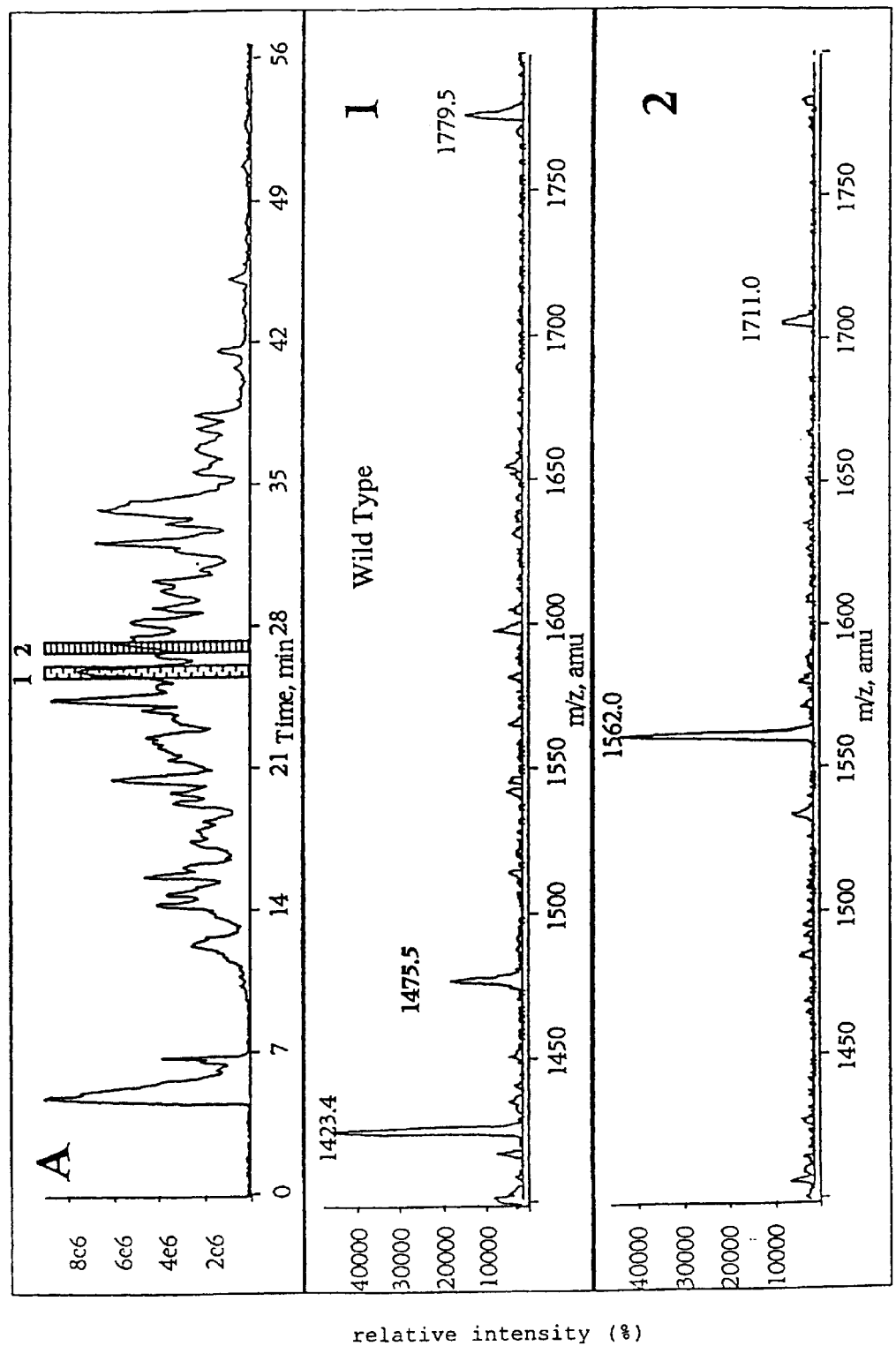

FIGS. 1a and 1b show the analysis of the peptide fragments of human cardiac β-myosin heavy chain (β-MHC) by means of a coupling of high performance liquid chromatography (HPLC) with mass spectrometry (MS). In this example, the presence of the heterozygotic mutant Val606Met, i.e., substitution of valin in position 606 of β-MHC, was looked for. FIG. 1a shows two marked ranges in which the fragment with a substituted amino acid and a molecular weight of 1507.5 could be detected in addition to the original fragment, the wild type fragment having a molecular weight of 1475.5, in a person for whom the substitution had been proven on the gene level. For comparison, FIG. 1b shows the analysis of a β-MHC sample of a person with no point mutation in this gene. In this case, only the wild type fragment can be detected; in the range in which the mutated fragment was eluted in FIG. 1a, this peptide is completely lacking. Thus, it becomes possible to detect mutated β-MHC in a person's muscle fibers.

In order to support this finding which is only substantiated by the observed shift in molecular weight of +32 by the amino acid substitution of Val by Met, fragments of an enzymatic cleavage were separated by HPLC, and the fractions were examined for the presence of peptides with molecular weights of 1475.5 and 1507.5 using mass spectrometry.

Figure 2B:
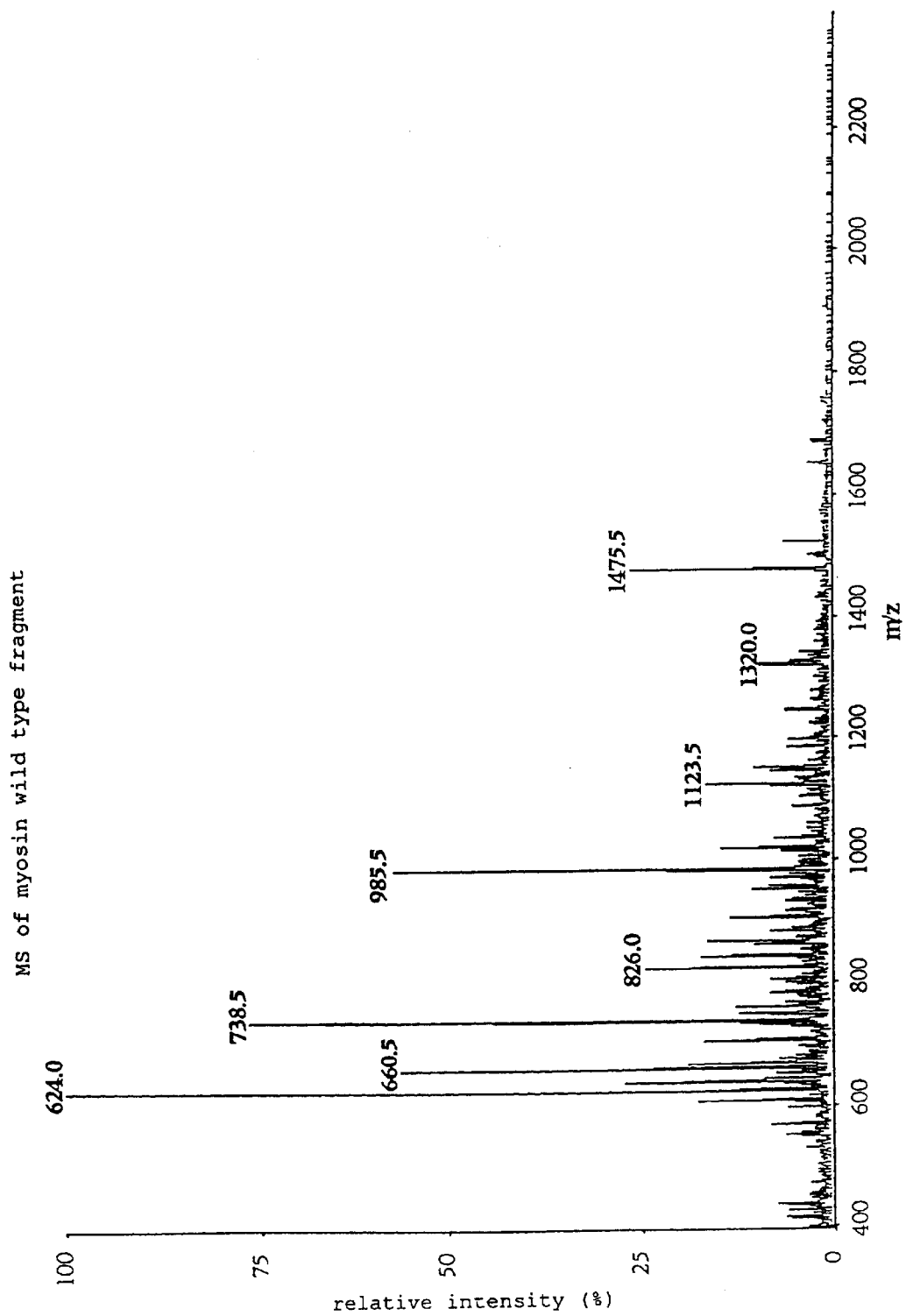

These peptides could be found in such fractions as corresponded to the above showed LC/MS analysis. FIGS. 2a and 2b show the mass spectra of these peptide fractions; in addition to the peptides to be detected, a large number of other peptides from β-MHC are also present.

The sequences of the peptides detected in the fractions were confirmed by collision-induced fragmentation by means of the coupling of two mass spectrometers (CID-MS/MS). The distances between the fragment ions designated as b and y correspond to the amino acids of the peptides with high specificity. From these distances, the sequence of the peptide can be established fully or in part. Problems are only encountered with the amino acids Leu and Ile which have no difference in molecular weight at all, and Lys and Gln which are different by only 0.04 unit masses. Since the enzymatic cleavage was performed with an enzyme which specifically cleaves behind Lys, the sequence determination can be based on the assumption that amino acids at the end of the peptide are Lys.

Figure 3B:
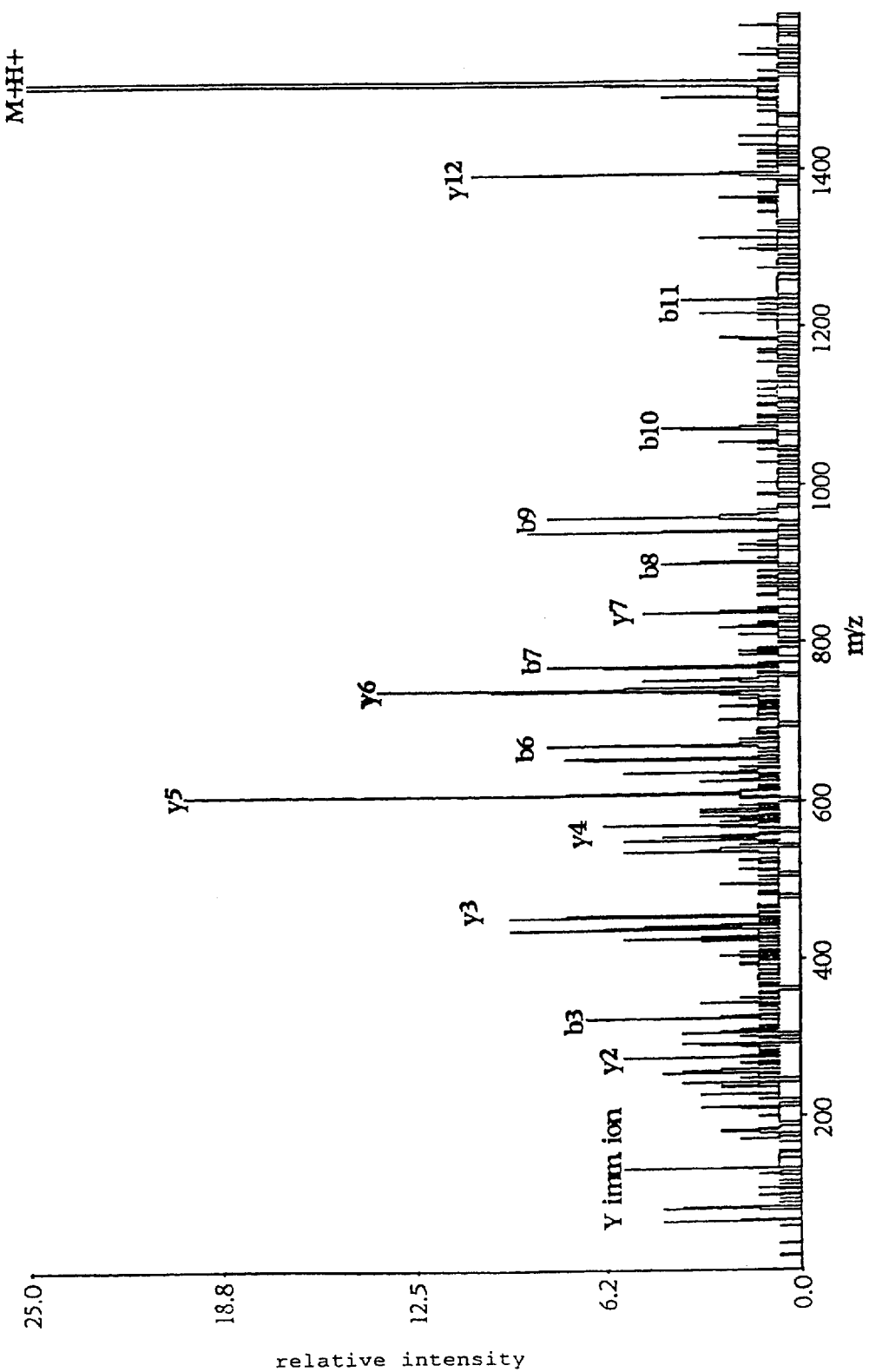

The CID-MS/MS spectra are shown in FIGS. 3a and 3b. The distance between b5 and b6 clearly shows the shift caused by the amino acid substitution while all other distances between the fragment ions remain unchanged. The evaluation yielded DPLNETVVGLYQK (SEQ ID No. 1) as the sequence for the wild type, and DPLNETVMGLYQK (SEQ ID No. 2) as the sequence for the mutant. Comparisons performed in data bases yielded no homology of the CID-MS/MS spectra with other proteins, except for very homologous β-MHCs from other species. Thus, the presence of the mutation in the muscle fibers could be clearly proven on a molecular level.

Figure 4A:
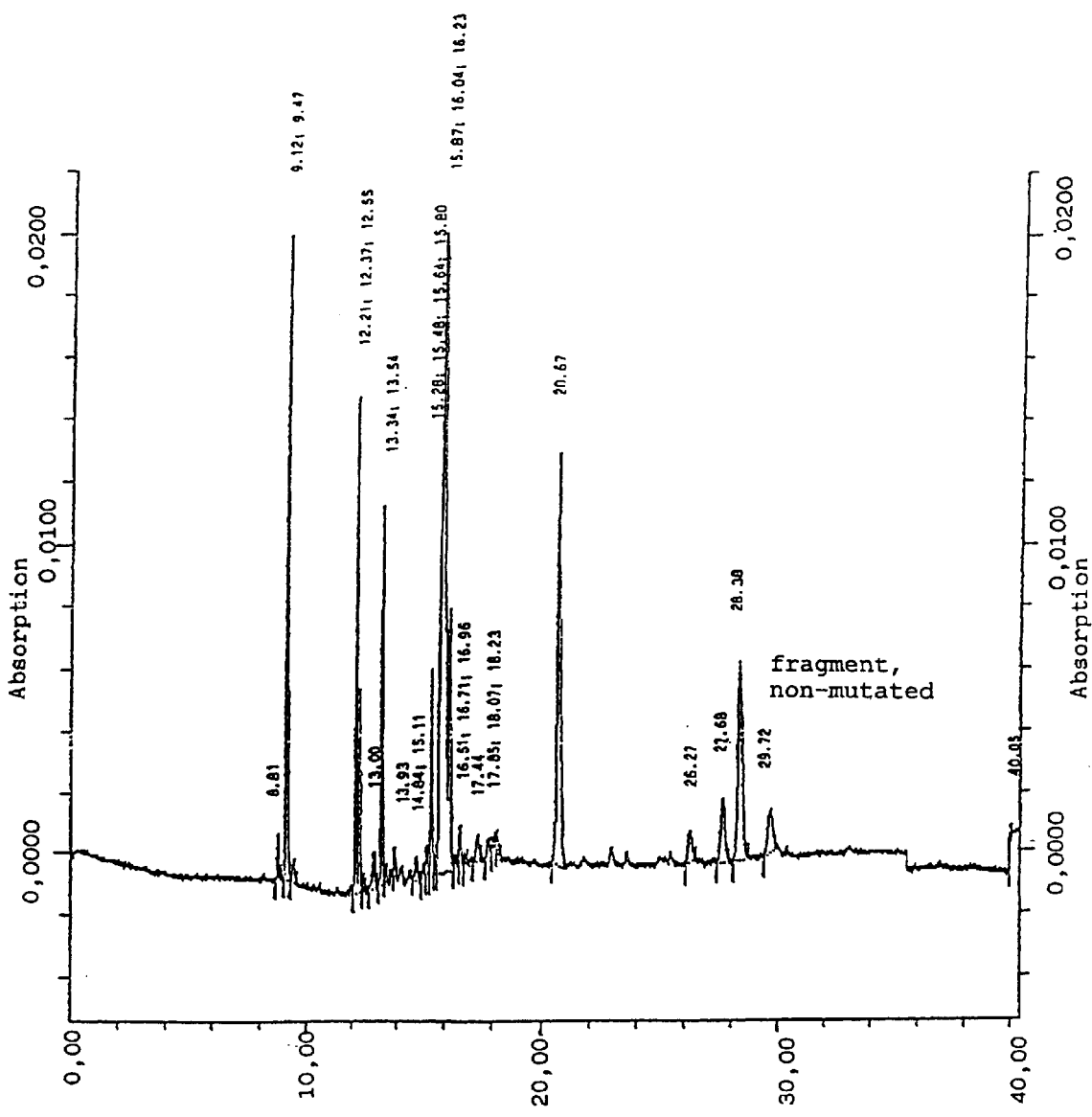
Figure 4B:
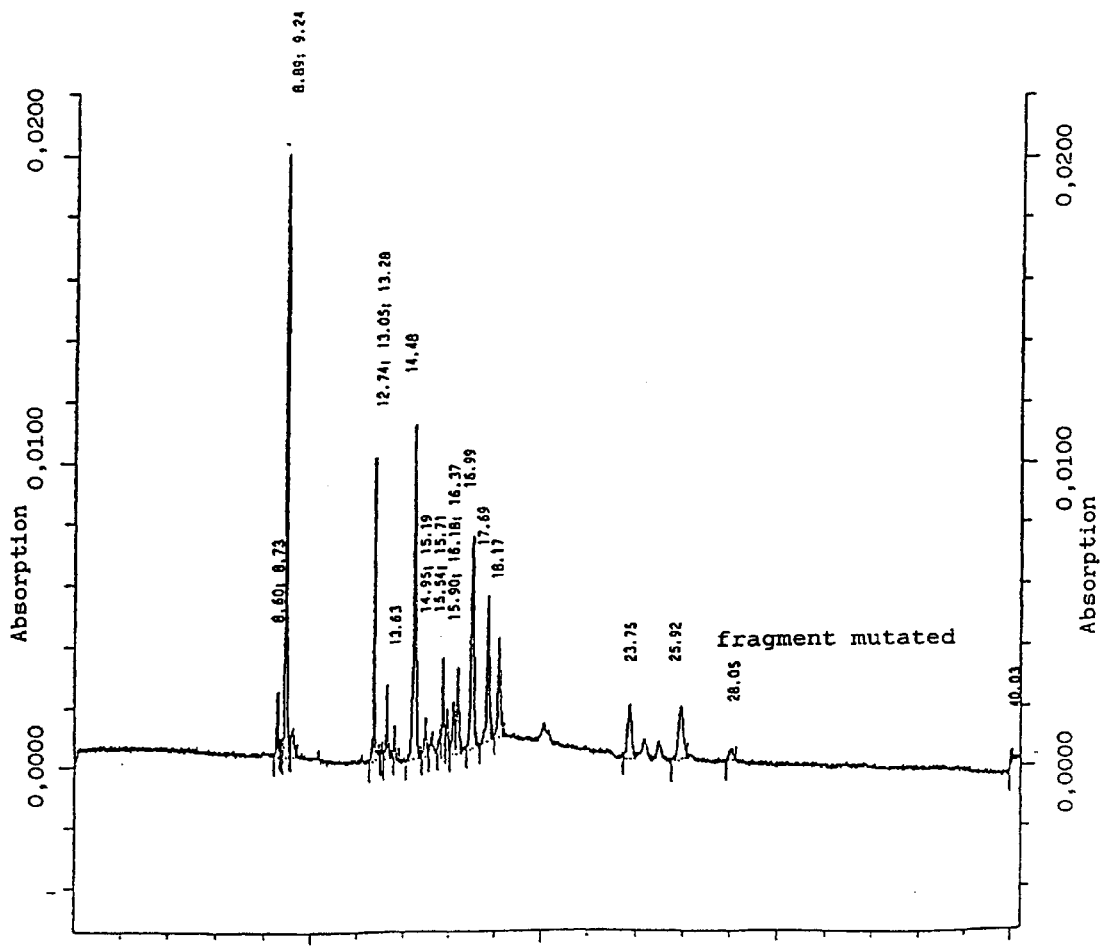

The stated techniques are not suitable for quantifying the degree of the incorporation of wild type to mutant. Because of the different ionization probabilities and the interference by other peptides present in the mixtures, the amount of peptide cannot be concluded from the results of mass spectrometry. For a quantification, another separation method is recommendable as a quantitative detection method, namely capillary zone electrophoresis. In this method which is based on other specific parameters than those of HPLC, peptides are separated in. unmodified glass capillaries, filled with buffers, with an inner diameter of 0.05 to 0.075 mm and a length of 50 cm in a strong electric field. The buffer employed has a pH value of 2.5 (100 mM phosphate buffer) in order to exclude electroendoosmotic fluxes of the buffer itself and to confer a positive charge to all peptides. In this system, the peptides of the identified fractions were separated. A commercially available peptide (low-pH mobility marker of Applied Biosystems) was added in the same amounts as an internal standard, in order to be able to compare, on one hand, the peak areas of the peptides to be compared, and to consider variations in the elution time in the different runs. The peptides to be detected themselves were identified in further separations by coinjection with a synthetic peptide of the same sequence. From the peak height and also from the peak area, a relative incorporation of the mutant of 10 to 15% of the total β-MHC was calculated. This experiment was performed with 5 different preparations, but from one patient. The thus measured values for the mutant β-MHV Val606Met were always between 10 and 15%. The capillary zone electrophoreses are shown in FIGS. 4a and 4b, the marked peptide (*) is the added internal standard, peptide (1) is the fragment of the wild type of the β-MHC, and peptide (2) is the fragment of the mutant of the β-MHC.

It is interesting that the sample examined does not show any symptoms of the familial hypertrophic cardiomyopathy. Therefore, it can be considered that a low degree of incorporation does not result in externally visible changes in muscle function.

The method according to the invention can-generally be applied to all mutants of the β-MHC. As yet, several fragments which are potential carriers of mutations were successfully identified; these fragments are underlined in FIG. 5, and the amino acids written below the continuous sequence are the as yet known substitutions. The method according to the invention can further be applied to all mutations having a pathogenic effect. For diagnostic purposes, this method may be used for the early recognition of the development of hereditary diseases;. in addition to gene analysis, a direct forecast of the risk of a severe disease or of the course of the disease can be made for every patient by analyzing the functioning proteins from the organism.

Example 1

LC/MS analysis of fragments of the heavy chain of the β-isoform of myosin (β-MHC) obtained with endoproteinase Lys-C The basis of the selective cleavage is the isolation of the β-MHC from muscle fibers of the soleus muscle which are obtained from biopsies by dissolution in a high salt buffer and precipitation of the β-MHC by decreasing the salt concentration. The collected β-MHC may be washed with water to remove disturbing soluble components.

For preparing the fragments to be analyzed, the precipitated β-MHC is slurried in 200 µl of 100 mM ammonium .hydrogencarbonate buffer, pH 8.2, and incubated with endoproteinase Lys-C (Boehringer Mannheim) at 37° C. for more than 24 hours. The solution is then subjected to freeze-drying, and the residue is dissolved in 100 µl of 0.1 M trifluoroacetic acid in water.

To remove undissolved components, the sample is filtered through an 0.2 µm cellulose acetate filter at a maximum of 10,000×g, and 20 to 50 µl aliquots are applied on the MB-HPLC column. The separation is performed through a reverse phase C18 column with an inner diameter of 1 mm and a length of 100 mm at a flow rate of 20 µl/min. The elution of the peptides is effected by a linear increase of 0.5%/min of the acetonitrile concentration in the buffer, from 10% acetonitrile in 0.06% TFA in water to 80% acetonitrile in 0.05% TFA in water. The eluting peptides are directed through a fused silica capillary and a UV detector directly into the electrospray ionization device of the quadrupole mass spectrometer (SCIEX API III, Perkin-Elmer, Langen). In the mass spectrometer, the m/z (mass to charge) values are determined over a range of from 400 to 2400 amu (atomic mass units) every 4.2 seconds. From the recorded total ion chromatogram and the respective mass spectra, the fragment of the wild type and of the mutant can be detected by computer aided evaluation.

After the separation described, a sample of the non-mutated β-MHC was analyzed together with the synthetic peptides having the sequences of the non-mutated and mutated fragments under the same conditions. The molecules which had been found are in the ranges in which the synthetic peptides are eluted.

FIG. 1: Top part: Total ion chromatogram of the separation of the fragments of the mutated β-MHC obtained with endoproteinase Lys-C.

Middle part: Detection of the non-mutated fragment in the cross-hatched range (1) of the top figure. The non-mutated fragment has a molecular weight of 1475.5 amu.

Bottom part: Detection of the mutated fragment in the crosshatched range (2) of the top figure. The mutated fragment has a molecular weight of 1507.5 amu.

EXAMPLE 2

Detection of the fragments of the wild type and the mutant of the β-MHC by means of the MALDI-MS technique As described in Example 1, the cleavage of the β-MHC was effected by incubation with endoproteinase Lys-C and a subsequent separation on a reverse phase C18 column under the conditions stated above. In this Example, instead of direct coupling with the mass spectrometer, an automated fraction collector collects fractions for 2 minutes each, and 0.5 µl each of these fractions is mixed with 1 µl of a suitable matrix substance, usually α-hydroxycinnamic acid or sinapic acid, dissolved in 60% acetonitrile and 0.2% TFA, on a support for MALDI-MS. The determination of the molecular weights is then performed in a MALDI-MS (Vestec, Houston) using an external standard, i.e., two known synthetic peptides, for calibrating the measurement.

In the corresponding fractions from Example 1, these measurements yielded the expected masses of 1477.5 and 1507.5 amu.

Thus, the mutated fragments can be unambiguously detected by means of MALDI-MS as well.

EXAMPLE 3

Analysis of the fractions from Example 2 by means of capillary electrophoresis

The fractions from Example 2 were separated by capillary electrophoresis (Beckmann P/ACE 2000, Beckmann, Munich) using fused silica capillaries with an inner diameter of 75 µm in a 100 mM sodium phosphate buffer, pH 8.0, at a voltage of 15 to 17 kV. The detection of the peptides was effected by means of a UV detector at 200 nm.

By coinjecting the synthetic peptides in a second separation run, the identity of the natural non-mutated and mutated fragments could be shown.

What is claimed is:

1. A method for the medical-diagnostic analysis of the expression and incorporation and of the ratio of wild type to mutant in different tissue and organ regions by comparing a deviation, caused by a mutation, of the amino acid composition of a protein to be examined expressed in the region of the mutation with a corresponding protein which is expressed by a wild type lacking the mutation, wherein
   a sample is taken from the organism at a site where the protein to be examined is expressed, is detected, and/or plays a physiological role;
   either the protein is concentrated or purified by methods of protein analysis, followed by a determination of its molecular weight, or
   a determination of the molecular weight of the protein to be examined is performed without a pretreatment of the sample;
   and the ratio of expression and incorporation of wild type to mutant is quantified.

2. The method according to claim 1, characterized in that the protein to be examined is cleaved into protein fragments.

3. The method according to claim 1, characterized in that the protein to be examined is the heavy chain of the β-isoform of myosin or a fragment thereof obtainable with endopeptidase Lys-C.

4. The method according to claim 1, characterized in that determining the molecular weight is effected by means of direct liquid chromatography-mass spectrometry coupling or indirect matrix-assisted laser desorption ionization mass spectrometry.

5. The method according to claim 1, for the medical-diagnostic quantification of the expression and incorporation of wild type and mutant in physiologically functional structures on the protein level.

6. The method according to claim 1, for the medical-diagnostic detection of as yet unknown pathogenic and non-pathogenic mutations directly on the protein level.

7. The method according to claim 1, wherein the ratio of expression and incorporation of wild type to mutant is quantified by capillary zone electrophoresis.

8. The method according to claim 7, characterized in that the protein to be examined is the cause for a disease that is caused by a heterozygote point mutation in the corresponding gene for that protein.

* * * * *

SEQUENCE LISTING

```
<160> NUMBER OF SEQ ID NOS:  3

<210> SEQ ID NO 1
<211> LENGTH: 1120
<212> TYPE: PRT
<213> ORGANISM: Homo sapiens
<220> FEATURE:
<221> NAME/KEY: MOD_RES
<222> LOCATION: (26)
<223> OTHER INFORMATION: "Xaa" represents Ala or Val
<221> NAME/KEY: MOD_RES
<222> LOCATION: (59)
<223> OTHER INFORMATION: "Xaa" represents Val or Ile
<221> NAME/KEY: MOD_RES
<222> LOCATION: (143)
<223> OTHER INFORMATION: "Xaa" represents Arg or Gln
<221> NAME/KEY: MOD_RES
<222> LOCATION: (249)
<223> OTHER INFORMATION: "Xaa" represents Arg or Gln
<221> NAME/KEY: MOD_RES
<222> LOCATION: (256)
<223> OTHER INFORMATION: "Xaa" represents Gly or Glu
<221> NAME/KEY: MOD_RES
<222> LOCATION: (403)
<223> OTHER INFORMATION: "Xaa" represents Arg, Gln, Leu or Trp
```

```
<221> NAME/KEY: MOD_RES
<222> LOCATION: (453)
<223> OTHER INFORMATION: "Xaa" represents Arg or Cys
<221> NAME/KEY: MOD_RES
<222> LOCATION: (513)
<223> OTHER INFORMATION: "Xaa" represents Phe or Cys
<221> NAME/KEY: MOD_RES
<222> LOCATION: (584)
<223> OTHER INFORMATION: "Xaa" represents Gly or Arg
<221> NAME/KEY: MOD_RES
<222> LOCATION: (587)
<223> OTHER INFORMATION: "Xaa" represents Asp or Val
<221> NAME/KEY: MOD_RES
<222> LOCATION: (602)
<223> OTHER INFORMATION: "Xaa" represents Asn or Ser
<221> NAME/KEY: MOD_RES
<222> LOCATION: (606)
<223> OTHER INFORMATION: "Xaa" represents Val or Met
<221> NAME/KEY: MOD_RES
<222> LOCATION: (615)
<223> OTHER INFORMATION: "Xaa" represents Lys or Asn
<221> NAME/KEY: MOD_RES
<222> LOCATION: (716)
<223> OTHER INFORMATION: "Xaa" represents Gly or Arg
<221> NAME/KEY: MOD_RES
<222> LOCATION: (719)
<223> OTHER INFORMATION: "Xaa" represents Arg or Trp
<221> NAME/KEY: MOD_RES
<222> LOCATION: (723)
<223> OTHER INFORMATION: "Xaa" represents Arg or Cys
<221> NAME/KEY: MOD_RES
<222> LOCATION: (731)
<223> OTHER INFORMATION: "Xaa" represents Pro or Leu
<221> NAME/KEY: MOD_RES
<222> LOCATION: (736)
<223> OTHER INFORMATION: "Xaa" represents Ile or Met
<221> NAME/KEY: MOD_RES
<222> LOCATION: (741)
<223> OTHER INFORMATION: "Xaa" represents Gly, Arg or Trp
<221> NAME/KEY: MOD_RES
<222> LOCATION: (778)
<223> OTHER INFORMATION: "Xaa" represents Asp or Gly
<221> NAME/KEY: MOD_RES
<222> LOCATION: (797)
<223> OTHER INFORMATION: "Xaa" represents Ala or Thr
<221> NAME/KEY: MOD_RES
<222> LOCATION: (870)
<223> OTHER INFORMATION: "Xaa" represents Arg or His
<221> NAME/KEY: MOD_RES
<222> LOCATION: (908)
<223> OTHER INFORMATION: "Xaa" represents Leu or Val
<221> NAME/KEY: MOD_RES
<222> LOCATION: (924)
<223> OTHER INFORMATION: "Xaa" represents Glu or Lys
<221> NAME/KEY: MOD_RES
<222> LOCATION: (935)
<223> OTHER INFORMATION: "Xaa" represents Glu or Lys
<221> NAME/KEY: MOD_RES
<222> LOCATION: (949)
<223> OTHER INFORMATION: "Xaa" represents Glu or Lys

<400> SEQUENCE: 1

Met Gly Asp Ser Glu Met Ala Val Phe Gly Ala Ala Pro Tyr Leu
 1               5                  10                  15

Arg Lys Ser Glu Lys Glu Arg Leu Glu Xaa Gln Thr Arg Pro Phe Asp
                20                  25                  30

Leu Lys Lys Asp Val Phe Val Pro Asp Asp Lys Gln Glu Phe Val Lys
            35                  40                  45

Ala Lys Ile Val Ser Arg Glu Gly Gly Lys Xaa Thr Ala Glu Thr Glu
        50                  55                  60

Tyr Gly Lys Thr Val Thr Val Lys Glu Asp Gln Val Met Gln Gln Asn
65                  70                  75                  80
```

```
Pro Pro Lys Phe Asp Lys Ile Glu Asp Met Ala Met Leu Thr Phe Leu
            85                  90                  95

His Glu Pro Ala Val Leu Tyr Asn Leu Lys Asp Arg Tyr Gly Ser Trp
        100                 105                 110

Met Ile Tyr Thr Tyr Ser Gly Leu Phe Cys Val Thr Val Asn Pro Tyr
        115                 120                 125

Lys Trp Leu Pro Val Tyr Thr Pro Glu Val Val Ala Ala Tyr Xaa Gly
        130                 135                 140

Lys Lys Arg Ser Glu Ala Pro His Ile Phe Ser Ile Ser Asp Asn
145                 150                 155                 160

Ala Tyr Gln Tyr Met Leu Thr Asp Arg Glu Asn Gln Ser Ile Leu Ile
                165                 170                 175

Thr Gly Glu Ser Gly Ala Gly Lys Thr Val Asn Thr Lys Arg Val Ile
                180                 185                 190

Gln Tyr Phe Ala Val Ile Ala Ala Ile Gly Asp Arg Ser Lys Lys Asp
                195                 200                 205

Gln Ser Pro Gly Lys Gly Thr Leu Glu Asp Gln Ile Ile Gln Ala Asn
        210                 215                 220

Pro Ala Leu Glu Ala Phe Gly Asn Ala Lys Thr Val Arg Asn Asp Asn
225                 230                 235                 240

Ser Ser Arg Phe Gly Lys Phe Ile Xaa Ile His Phe Gly Ala Thr Xaa
                245                 250                 255

Lys Leu Ala Ser Ala Asp Ile Glu Thr Tyr Leu Leu Glu Lys Ser Arg
                260                 265                 270

Val Ile Phe Gln Leu Lys Ala Glu Arg Asp Tyr His Ile Phe Tyr Gln
                275                 280                 285

Ile Leu Ser Asn Lys Lys Pro Glu Leu Leu Asp Met Leu Leu Ile Thr
        290                 295                 300

Asn Asn Pro Tyr Asp Tyr Ala Phe Ile Ser Gln Gly Glu Thr Thr Val
305                 310                 315                 320

Ala Ser Ile Asp Asp Ala Glu Glu Leu Met Ala Thr Asp Asn Ala Phe
                325                 330                 335

Asp Val Leu Gly Phe Thr Ser Glu Glu Lys Asn Ser Met Tyr Lys Leu
                340                 345                 350

Thr Gly Ala Ile Met His Phe Gly Asn Met Lys Phe Lys Leu Lys Gln
                355                 360                 365

Arg Glu Glu Gln Ala Glu Pro Asp Gly Thr Glu Ala Asp Lys Ser
        370                 375                 380

Ala Tyr Leu Met Gly Leu Asn Ser Ala Asp Leu Leu Lys Gly Leu Cys
385                 390                 395                 400

His Pro Xaa Val Lys Val Gly Asn Glu Tyr Val Thr Lys Gly Gln Asn
                405                 410                 415

Val Gln Gln Val Ile Tyr Ala Thr Gly Ala Leu Ala Lys Ala Val Tyr
                420                 425                 430

Glu Arg Met Phe Asn Trp Met Val Thr Arg Ile Asn Ala Thr Leu Glu
                435                 440                 445

Thr Lys Gln Pro Xaa Gln Tyr Phe Ile Gly Val Leu Asp Ile Ala Gly
        450                 455                 460

Phe Glu Ile Phe Asp Phe Asn Ser Phe Glu Gln Leu Cys Ile Asn Phe
465                 470                 475                 480

Thr Asn Glu Lys Leu Gln Gln Phe Phe Asn His His Met Phe Val Leu
                485                 490                 495
```

-continued

```
Glu Gln Glu Glu Tyr Lys Lys Glu Gly Ile Glu Trp Thr Phe Ile Asp
            500                 505                 510

Xaa Gly Met Asp Leu Gln Ala Cys Ile Asp Leu Ile Glu Lys Pro Met
            515                 520                 525

Gly Ile Met Ser Ile Leu Glu Glu Cys Met Phe Pro Lys Ala Thr
            530                 535                 540

Asp Met Thr Phe Lys Ala Lys Leu Phe Asp Asn His Leu Gly Lys Ser
545                 550                 555                 560

Ala Asn Phe Gln Lys Pro Arg Asn Ile Lys Gly Lys Pro Glu Ala His
                565                 570                 575

Phe Ser Leu Ile His Tyr Ala Xaa Ile Val Xaa Tyr Asn Ile Ile Gly
            580                 585                 590

Trp Leu Gln Lys Asn Lys Asp Pro Leu Xaa Glu Thr Val Xaa Gly Leu
        595                 600                 605

Tyr Gln Lys Ser Ser Leu Xaa Leu Leu Ser Thr Leu Phe Ala Asn Tyr
        610                 615                 620

Ala Gly Ala Asp Ala Pro Ile Glu Lys Gly Lys Gly Lys Ala Lys Lys
625                 630                 635                 640

Gly Ser Ser Phe Gln Thr Val Ser Ala Leu His Arg Glu Asn Leu Asn
                645                 650                 655

Lys Leu Met Thr Asn Leu Arg Ser Thr His Pro His Phe Val Arg Cys
            660                 665                 670

Ile Ile Pro Asn Glu Thr Lys Ser Pro Gly Val Met Asp Asn Pro Leu
        675                 680                 685

Val Met His Gln Leu Arg Cys Asn Gly Val Leu Glu Gly Ile Arg Ile
        690                 695                 700

Cys Arg Lys Gly Phe Pro Asn Arg Ile Leu Tyr Xaa Asp Phe Xaa Gln
705                 710                 715                 720

Arg Tyr Xaa Ile Leu Asn Pro Ala Ala Ile Xaa Glu Gly Gln Phe Xaa
            725                 730                 735

Asp Ser Arg Lys Xaa Ala Glu Lys Leu Leu Ser Ser Leu Asp Ile Asp
            740                 745                 750

His Asn Gln Tyr Lys Phe Gly His Thr Lys Val Phe Phe Lys Ala Gly
        755                 760                 765

Leu Leu Gly Leu Leu Glu Glu Met Arg Xaa Glu Arg Leu Ser Arg Ile
770                 775                 780

Ile Thr Arg Ile Gln Ala Gln Ser Arg Gly Val Leu Xaa Arg Met Glu
785                 790                 795                 800

Tyr Lys Lys Leu Leu Glu Arg Arg Asp Ser Leu Leu Val Ile Gln Trp
            805                 810                 815

Asn Ile Arg Ala Phe Met Gly Val Lys Asn Trp Pro Trp Met Lys Leu
            820                 825                 830

Tyr Phe Lys Ile Lys Pro Leu Leu Lys Ser Ala Glu Arg Glu Lys Glu
            835                 840                 845

Met Ala Ser Met Lys Glu Glu Phe Thr Arg Leu Lys Glu Ala Leu Glu
            850                 855                 860

Lys Ser Glu Ala Arg Xaa Lys Glu Leu Glu Glu Lys Met Val Ser Leu
865                 870                 875                 880

Leu Gln Glu Lys Asn Asp Leu Gln Leu Gln Val Gln Ala Glu Gln Asp
                885                 890                 895

Asn Leu Ala Asp Ala Glu Glu Arg Cys Asp Gln Xaa Ile Lys Asn Lys
            900                 905                 910
```

-continued

```
Ile Gln Leu Glu Ala Lys Val Lys Glu Met Asn Xaa Arg Leu Glu Asp
        915                 920                 925

Glu Glu Glu Met Asn Ala Xaa Leu Thr Ala Lys Lys Arg Lys Leu Glu
        930                 935                 940

Asp Glu Cys Ser Xaa Leu Lys Arg Asp Ile Asp Asp Leu Glu Leu Thr
945                 950                 955                 960

Leu Ala Lys Val Glu Lys Glu Lys His Ala Thr Glu Asn Lys Val Lys
                965                 970                 975

Asn Leu Thr Glu Glu Met Ala Gly Leu Asp Glu Ile Ile Ala Lys Leu
            980                 985                 990

Thr Lys Glu Lys Lys Ala Leu Gln Glu Ala His Gln Gln Ala Leu Asp
        995                 1000                1005

Asp Leu Gln Ala Glu Glu Asp Lys Val Asn Thr Leu Thr Lys Ala Lys
    1010                1015                1020

Val Lys Leu Glu Gln Gln Val Asp Asp Leu Glu Gly Ser Leu Glu Gln
1025                1030                1035                1040

Glu Lys Lys Val Arg Met Asp Leu Glu Arg Ala Lys Arg Lys Leu Glu
                1045                1050                1055

Gly Asp Leu Lys Leu Thr Gln Glu Ser Ile Met Asp Leu Glu Asn Asp
            1060                1065                1070

Lys Gln Gln Leu Asp Glu Arg Leu Lys Lys Lys Asp Phe Glu Leu Asn
        1075                1080                1085

Ala Leu Asn Ala Arg Ile Glu Asp Glu Gln Ala Leu Gly Ser Gln Leu
    1090                1095                1100

Gln Lys Lys Leu Lys Glu Leu Gln Ala Arg Ile Glu Glu Leu Glu Glu
1105                1110                1115                1120

<210> SEQ ID NO 2
<211> LENGTH: 13
<212> TYPE: PRT
<213> ORGANISM: Homo sapiens

<400> SEQUENCE: 2

Asp Pro Leu Asn Glu Thr Val Val Gly Leu Tyr Gln Lys
 1               5                  10

<210> SEQ ID NO 3
<211> LENGTH: 13
<212> TYPE: PRT
<213> ORGANISM: Homo sapiens

<400> SEQUENCE: 3

Asp Pro Leu Asn Glu Thr Val Met Gly Leu Tyr Gln Lys
 1               5                  10
```